(12) United States Patent
Li

(10) Patent No.: US 9,994,892 B2
(45) Date of Patent: *Jun. 12, 2018

(54) INSTANTANEOUS DETECTION OF BIOMARKS AND USES THEREOF

(71) Applicant: Zhong Li, Short Hills, NJ (US)

(72) Inventor: Zhong Li, Short Hills, NJ (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/673,634

(22) Filed: Aug. 10, 2017

(65) Prior Publication Data

US 2017/0342472 A1     Nov. 30, 2017

Related U.S. Application Data

(63) Continuation of application No. 14/548,940, filed as application No. PCT/US2013/043295 on May 30, 2013, now Pat. No. 9,765,386.

(60) Provisional application No. 61/652,918, filed on May 30, 2012.

(51) Int. Cl.
| | |
|---|---|
| *C12Q 1/68* | (2018.01) |
| *G01N 33/543* | (2006.01) |
| *B82Y 5/00* | (2011.01) |
| *B82Y 15/00* | (2011.01) |

(52) U.S. Cl.
CPC ............ *C12Q 1/6834* (2013.01); *B82Y 5/00* (2013.01); *C12Q 1/6813* (2013.01); *G01N 33/54333* (2013.01); *B82Y 15/00* (2013.01)

(58) Field of Classification Search
CPC ............................ C12Q 1/6813; C12Q 1/6834
USPC ........................................................ 506/9
See application file for complete search history.

(56) References Cited

U.S. PATENT DOCUMENTS

| 4,672,040 | A | 6/1987 | Josephson |
| 6,852,493 | B2 | 2/2005 | Ramirez-Vick et al. |
| 7,459,145 | B2 | 12/2008 | Bao et al. |
| 7,902,122 | B2 | 3/2011 | Jung et al. |
| 2002/0119470 | A1 | 8/2002 | Nerenberg et al. |
| 2002/0164607 | A1 | 11/2002 | Ramirez-Vick et al. |
| 2007/0254372 | A1* | 11/2007 | Bickel ............... B01L 3/502715 436/86 |
| 2009/0170212 | A1 | 7/2009 | Van Der Wijk |
| 2010/0291710 | A1 | 11/2010 | Ovsyanko |
| 2011/0159484 | A1 | 6/2011 | Rhee et al. |
| 2012/0295366 | A1 | 11/2012 | Zilch et al. |

FOREIGN PATENT DOCUMENTS

| CN | 101925818 | 12/2010 |
| EP | 1 206 572 B1 | 5/2002 |
| WO | WO 00/73506 A1 | 12/2000 |
| WO | WO 2011/080068 A1 | 7/2011 |
| WO | WO 2012/055069 A1 | 5/2012 |

OTHER PUBLICATIONS

Almadidy et al., Analytica Chimica Acta 461:37-47 (2002).
Arlett et al., Nature Nanotechnology 6:203-15 (2011).
Aslan et al., Journal of Immunological Methods, 331:103-13 (2008).
Belosludtsev et al., Biochemical and Biophysical Research Communications, 282:1263-67 (2001).
Chinese Office Action dated Jun. 19, 2015 for Chinese Application No. 201380027910.2 with English Translation.
Dave and Liu, J. Phys. Chem B, 114:15694-99 (2010).
Diaz and Barisone, Journal of Visualized Experiments, 1-4 (2011).
Extended European Search Report dated Jan. 22, 2016 for European Application No. 13796774.1.
Ferreira et al., "Rapid DNA hybridization based on ac field focusing of magnetically labeled target DNA," Jun. 29, 2005, pp. 013901, vol. 87(1), Applied Physics Letters, American Institute of Physics, Melville, NY (abstract only).
Ferreira et al., Applied Physics Letters, 87:013901-1-013901-3 (2005).
Gantelius, Thesis, Royal Institute of Technology, Stockholm, Sweden, pp. I-XII and 1-102, (2009).
Ghindilis et al., Electroanalysis 21(13):14459-68 (2009).
Graham et al., Trends in Biotechnology, 22(9):455-62 (2004).
Hsieh et al., Microfluid Nanofluid, 6:391-401(2009).
Kuo et al., Nature Biotechnology, 24(7):832-40 (2006).
Kuo, Expression Measurement Comparison between Microarray Platforms, 15 pages (2006).
Mogi et al., Biosensors and Bioelectronics, 26:1942-46 (2011).
PCT/US2013/043295 International Search Report dated Sep. 19, 2013 by S. Ilchenko.
Rao et al., Anal Chem, 84(21):9379-87 (2012).
Relógio et al., Nucleic Acids Research, 30(11):1-10 (2002).
Sheykoplyas et al., Lab on a Chip, 7:1294-1302 (2007).
Stahl et al., Genomics 90:741-45 (2007).
Wang and Li, IEEE Transactions on Magnetics 44(7):1687-1702 (2008).
Wang et al., Talanta 84:565-71 (2011).

* cited by examiner

*Primary Examiner* — Karla A Dines
(74) *Attorney, Agent, or Firm* — RatnerPrestia

(57) ABSTRACT

The present invention relates to a novel method for detecting instantaneously a biomarker immobilized to a solid surface and related uses. The method comprises exposing the biomarker to a probe having a magnetic label in a solution; applying a magnetic field to the solution, whereby a complex of the biomarker and the probe is formed on the solid surface; withdrawing the magnetic field; removing the solution from the solid surface; and detecting the complex instantaneously, wherein the presence of the complex on the solid surface indicates the presence of the biomarker.

20 Claims, 3 Drawing Sheets

FIGURE 1

| T1 | T2 | T3 | T4 | Code |
|----|----|----|----|------|
| ● | ● | ○ | ● | 1101 |
| ● | ○ | ● | ● | 1011 |
| ○ | ● | ○ | ● | 0101 |
| ● | ○ | ● | ○ | 1010 |
| ● | ● | ● | ○ | 1110 |
| ● | ● | ○ | ● | 1101 |
| ○ | ● | ● | ○ | 0110 |
| ● | ○ | ○ | ● | 1001 |

INSTANTANEOUS DETECTION OF BIOMARKS AND USES THEREOF

CROSS-REFERENCE TO RELATED APPLICATION

This application is a continuation of U.S. application Ser. No. 14/548,940, filed Nov. 20, 2014, which is a U.S. National Phase Application of International Application No. PCT/US2013/043295, filed May 30, 2013, which claims the benefit of U.S. Provisional Application No. 61/652,918, filed May 30, 2012, the contents of each of which are incorporated herein by reference in their entireties for all purposes.

FIELD OF THE INVENTION

The present invention relates generally to methods for instantaneous detection of biomarkers and uses thereof.

BACKGROUND OF THE INVENTION

Detection of biomarkers (e.g., nucleic acid molecules, amino acid molecules or cells) by using probes (e.g., complementary nucleic acid molecules or antibodies) having high binding affinity with the biomarkers has been routinely used in biomedical research labs and clinical diagnostics. They usually require rather long incubation time for the binding and lengthy protocols to ensure sufficient sensitivity and specificity for the detection.

The average single-base-pair hybridization and dehybridization rates in a duplex DNA formation are on the order of a millisecond. One rate limiting step, however, is for two complementary oligonucleotides to collide with each other and initiate the base pairing process. Surface-bound oligonucleotides also behave differently than oligonucleotides in a solution. A large body of literature has shown that hybridization that occurs in the interface between a solid and a solution (i.e., surface-based hybridization) exhibits substantially different hybridization kinetics than that observed in bulk solutions. Surface-based hybridization may occur via either of two mechanisms: direct hybridization from the bulk phase (i.e., 3D diffusion) or hybridization after an initial nonspecific adsorption step followed by subsequent surface diffusion to the probe (i.e., 2D diffusion). Modeling supported by experimental data has shown that the two-step mechanism involving 2D diffusion is several magnitudes faster than the direct hybridization mechanism with a proper target density and a probe concentration. In the two-step mechanism, the surface diffusion step, following the second order Langmuir model, is a rate-limiting step for efficient hybridization, since the initial adsorption are normally completed in milliseconds.

Paramagnetic agents have been used to label biomolecules for concentrating the labeled biomolecules when a magnetic field is applied. However, the paramagnetic agents are much larger than DNA probes, limiting the accessibility of labeled DNA probe to immobilized target DNA molecules and saturating the surface for hybridization. International Patent Application No. PCT/US00/14969 (published as WO 00/73506) discloses that the use of a probe attached to superparamagnetic particles having a diameter of about 1-10 nanometers reduces the hybridization time from days to minutes.

There remains a need for reliable and sensitive methods to detect biomarkers instantaneously.

SUMMARY OF THE INVENTION

The present invention relates to methods for detecting instantaneously a biomarker immobilized to a solid surface and related kits and devices.

A method for detecting instantaneously a biomarker immobilized to a solid surface is provided. The method comprises:

(a) exposing the biomarker to a probe having a magnetic label in a solution;

(b) applying a magnetic field to the solution, whereby a complex of the biomarker and the probe is formed on the solid surface;

(c) withdrawing the magnetic field;

(d) removing the solution from the solid surface; and (e) detecting the complex instantaneously, wherein the presence of the complex on the solid surface indicates the presence of the biomarker.

The biomarker may comprise a target polynucleotide having a first nucleotide sequence, and the probe may be a polynucleotide probe comprising a second nucleotide sequence, which is complementary with the first nucleotide sequence. The complex may comprise a hybrid of the target polynucleotide and the polynucleotide probe.

The target polynucleotide may be a single stranded DNA or RNA, preferably DNA. The target polynucleotide may comprise 8-50 nucleotides.

The biomarker may comprise a target polypeptide, and the probe may be a polypeptide probe that binds specifically to the target polypeptide. The polypeptide probe may be an antibody that binds specifically to the target polypeptide.

The probe may be attached to a particle comprising a magnetic material. The particle may have a diameter of about 1 µm. The probe may be attached to the particle via a linker. The probe may be biotinylated, and the particle may be a streptavidin-coated superparamagnetic bead.

The magnetic field may be applied horizontally or vertically across the solid surface, or in a uniform fashion over the solid surface. Preferably, the magnetic field is applied horizontally across the solid surface. The magnetic field may be applied for no more than 5 seconds.

The complex may be detected visually. The biomarker may be detected no more than 5 seconds after exposing the biomarker to the probe.

The biomarker may be obtained from a biological sample. The biomarker may be on a product, which may be a pharmaceutical product. The pharmaceutical product may be a drug. The instantaneous detection method of the present invention may further comprise authenticating the product, wherein the presence of the biomarker on the product indicates that the product is authentic.

BRIEF DESCRIPTION OF THE DRAWINGS

FIG. 1 shows an array of spots represented by filled and unfilled circles. Spots in each column contain the same target oligonucleotide T1, T2, T3 or T4 as indicated on top of each column. While a filled circle represents the presence of the target oligonucleotide, an unfilled circle represents the absence of the corresponding target oligonucleotide. The presence or absence of the target oligonucleotides in each row of the spots constitutes a code indicated to the right of the row.

DETAILED DESCRIPTION OF THE INVENTION

Figure 2:
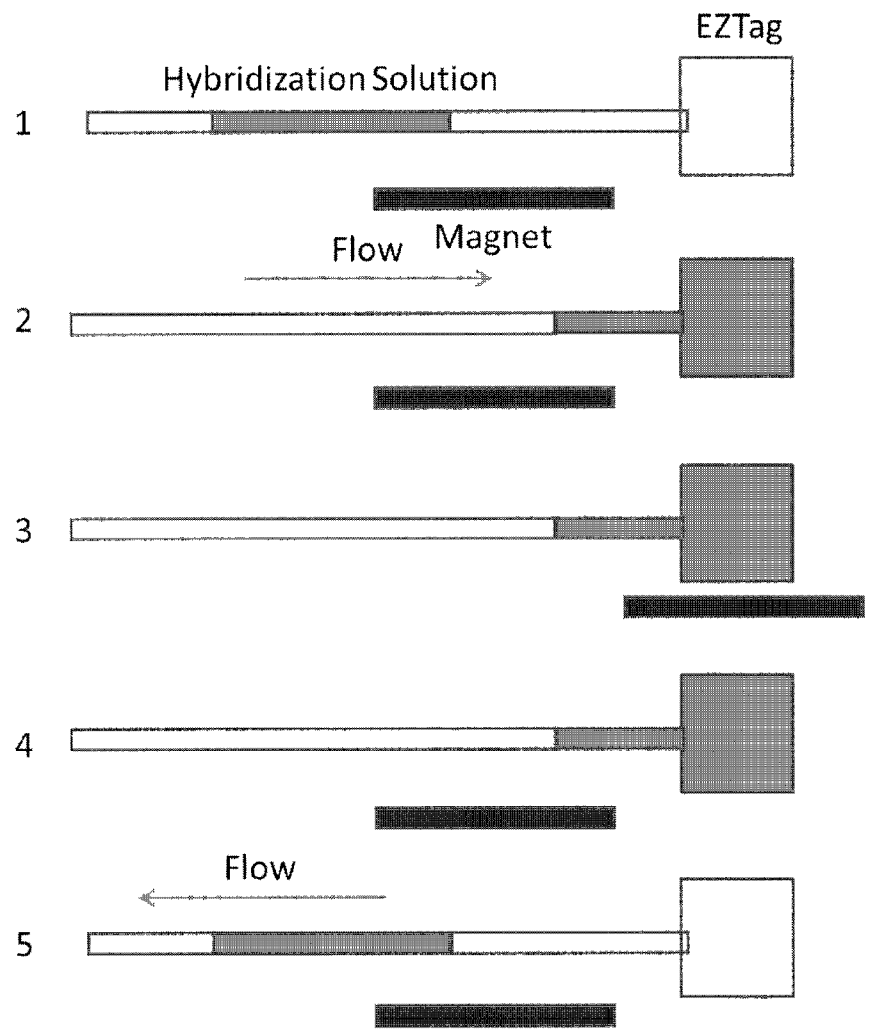
FIG. 2 is a schematic diagram illustrating the movement of a hybridization solution comprising magnetically labeled probes in a channel connected with a chamber comprising an EZTag having an array of spots each containing a target oligonucleotide, in response to a magnetic field created by a magnet for DNA hybridization. Step 1: The magnet is placed away from the chamber and the hybridization solution is away from the chamber; Step 2: The hybridization solution flows towards the EZTag and fills the chamber; Step 3: The magnet is placed under the chamber, and the target oligonucleotides in EZTag are exposed to the probes in the hybridization solution such that DNA hybridization occurs; Step 4: The magnet is moved away from the chamber; Step 5: The hybridization solution flows away from the chamber, leaving only magnetic probes bound to the target oligonucleotides on the EZTag.

The present invention relates to a novel method for detecting instantaneously a biomarker immobilized to a solid surface. In particular, a magnetically labeled probe is used to form a complex with the biomarker instantaneously in the presence of a magnetic field. The present method does not involve amplification of the biomarker or washing the complex before detecting the complex of the biomarker and the probe.

The present invention provides a method for detecting a biomarker instantaneously. The biomarker is immobilized to a solid surface. The method comprises exposing the biomarker to a probe having a magnetic label in a solution; applying a magnetic field to the solution, whereby a complex of the biomarker and the probe is formed on the solid surface; withdrawing the magnetic field; removing the solution from the solid surface; and detecting the complex instantaneously. The presence of the complex on the solid surface indicates the presence of the biomarker.

The term "biomarker" as used herein refers to a naturally occurring or man-made artificial material, for example, recombinantly or chemically, comprising a target biological molecule, chemical compound, cell, or tissue. Examples of the biomarkers include polynucleotides, polypeptides, polysaccharides, antibodies, monoclonal antibodies, cell membrane receptors, cofactors, sugars, lectins, cells, cellular membrane, and drugs. The biomarker may comprise one or more target polynucleotides or one or more target polypeptides.

The biomarker may be isolated from a sample. The sample may be a biological sample or an environmental sample. A biological sample is obtained from a biological source, for example, an organism such as a microorganism, animal or plant, preferably a mammal, more preferably a human. Examples of biological samples include blood, serum, ascites fluid, cerebrospinal fluid, amniotic fluid, synovial fluid, pleural fluid, saliva, sputum, stool, urine, semen, tissue, biopsies, swabs, and the like from human and non-human sources. An environmental sample is obtained from an environmental source such as air, water, soil, and environments exposed to extremes of conditions (e.g., temperature or pressure). Environmental samples may include samples from industrial processes. The biomarker may also be present as an identification or authentication tag in a product, for example, a biological or pharmaceutical drug, or other commercial products such as clothing, handbags, shoes and automobiles.

The term "polynucleotide" as used herein refers a polymer of nucleotides of any length. A polynucleotide may be an oligonucleotide having fewer than 100 nucleotides. The polynucleotide may be any type of single stranded of DNA, cDNA, RNA, or a combination or derivative thereof. The polynucleotide may be a peptide nucleic acid (PNA). The polynucleotide may be linear or circular, preferably linear. A double stranded DNA may be converted into a single stranded DNA for use in the detection method according to the present invention. A polynucleotide may have about 5-1000, 5-100, 5-50, 8-50, 10-40, 20-40 or 8-25 nucleotides, for example, about 8, 24 or 50 nucleotides.

The term "complementary" as used herein refers to the ability of two single stranded polynucleotides, either two DNA strands or a DNA strand and a RNA strand, to form a double stranded duplex having, for example, at least about 80%, 90%, 95%, or 99%, preferably at least about 90%, more preferably at least about 95%, most preferably about 100%, matching purine bases and pyrimidine bases. Two complementary polynucleotides may have fewer than about 5, 4, 3, 2 or 1 base mismatches.

The term "hybridization" as used herein refers to the process in which two single stranded complementary polynucleotides bind non-covalently to form a stable double stranded polynucleotide, also known as a hybrid. The two single stranded polynucleotides may be complementary with each other perfectly, i.e., having 100 % matching bases, or partially or less than 100% matching bases, e.g., having at least about 80%, 90%, 95% or 99% matching bases. The degree of hybridization is the proportion of single stranded polynucleotides that form stable hybrids, which may be at least about 50%, 60%, 70%, 80%, 90%, 95% or 99%, preferably at least about 90%, more preferably at least about 95%. Hybridization conditions can be chosen by a skilled practitioner to provide a desired degree of sequence specific hybridization. In various embodiments, one or more base mismatches may be permitted, or perfect complementarity may be required. In the detection method of the present invention, the degree of hybridization is the proportion of the target polynucleotides that form stable hybrids with the polynucleotide probes, which may be at least about 50%, 60%, 70%, 80%, 90%, 95% or 99%, preferably at least about 90%, more preferably at least about 95%.

A nucleotide may be synthesized or modified from a naturally occurring nucleotide, for example, a methylated nucleotide or nucleotide analog. A modified nucleotide may have sufficient structural features in common with a naturally occurring nucleotide such that, when incorporated into a polynucleotide sequence, it allows hybridization with a naturally occurring nucleotide sequence in solution. One or more nucleotides in a polynucleotide may be modified to stabilize or destabilize hybrid formation or to enhance the specificity of hybridization with a complementary polynucleotide as desired.

The term "specificity of hybridization" as used herein refers to the degree of matching bases in a hybrid. The specification of hybridization in the detection method of the present invention may have at least about 80%, 90%, 95%, 99% or 100% matching bases, preferably at least about 90%, more preferably at least about 95%, most preferably about 100% matching bases, in the hybrid of the target polynucleotide and the polynucleotide probe.

The terms "polypeptide" and "protein" are used herein interchangeably, and refer to a polymer of amino acids of any length. The polypeptide may have about 5-1000, 10-100, 10-50, 10-40, or 10-20 amino acids. An amino acid may be modified from a naturally occurring amino acid by, for example, glycosylation or phosphorylation. In some embodiments, one or more amino acids in the target polypeptide may be modified to stabilize or destabilize the binding complex formation between the target polypeptide and the polypeptide probe, or to enhance the specificity of binding with the polypeptide probe.

The solid surface may be any solid surface suitable for attachment of the biomarker. The solid surface may be made from one or more materials selected from the group consisting of polymers, plastics, resins, polysaccharides, silica or silica-based materials, carbon, metals, inorganic glasses, and membranes. The solid surface may be flat or curved. The solid surface may be separated into different regions, for example, wells. The solid surface may also be in the form of beads, resins, gels, microspheres, or other geometric configurations.

The biomarker may be attached to the solid surface directly via a covalent or non-covalent bond, preferably a covalent bond. The biomarker may also be attached to the solid surface indirectly, for example, via a linker, which may be cleavable. For example, the linker may be selected from the group consisting of biotin-streptavidin, Acrydite-SH, COOH—NH2, NH2-COOH, OH—BrCN, disulfide bond, Hydrazide-ligand with oxidized carbohydrate, protein A-antibody such as IgG, anti-mouse IgG-mouse IgG, and cleavable conjugating molecules.

The term "probe" as used herein refers to an agent capable of binding to a biomarker specifically. Where the biomarker comprises a target polynucleotide, the probe may be a polynucleotide probe having a nucleotide sequence complementary with the nucleotide sequence of the target polynucleotide, and a hybrid of the target polynucleotide and the polynucleotide probe may be formed on the solid surface. The polynucleotide probe may be an oligonucleotide having about 5-100, 5-50 or 10-25 nucleotides, and may be linear or circular, preferably linear.

Where the biomarker comprises a target polypeptide, the probe may be a polypeptide probe that binds specifically to the target polypeptide. The polypeptide probe may comprise about 5-1000, 10-100, 10-50, 10-40, or 10-20 amino acids. The probe may be an antibody or a single-chain variable fragment that binds specifically to the target polypeptide. The term "antibody" as used herein includes whole antibodies, antigen binding fragments (or antigen-binding portions), and single chains thereof. A whole antibody refers to a glycoprotein typically having two heavy chains and two light chains, and includes an antigen binding portion. The term "antigen binding portion" of an antibody as used herein refers to one or more fragments of the antibody that retain the ability of specifically binding to an antigen. The term "single-chain variable fragment" of an antibody as used herein refers to a fusion protein of the variable regions of the heavy and light chains of the antibody, connected with a short linker peptide, for example, of about 20-25 amino acids, that retains the ability of specifically binding to an antigen.

The term "magnetic label" as used herein refers to a moiety attached to the probe, directly or indirectly, that is capable of moving the probe in response to a magnetic field. The magnetic label may be a particle (e.g., bead) comprising a magnetic material, and may be magnetic, paramagnetic, superparamagnetic, ferromagnetic, or diamagnetic. The particle may be made of any inert material known in the art, for example, plastic, metal, glass and ceramic, and have of any shape, preferably round. The magnetic particle may have a diameter ranging from about 1 nm to about 100 μm, from about 500 nm to about 10 μm, from about 750 nm to about 5 μm, or from about 900 nm to about 2 μm, preferably about 1 μm.

The probe may be attached to a magnetic particle via a linker. The linker may be any material capable of binding the probe specifically, but not the biomarker, for example, a capture probe, biotin-streptavidin, Acrydite-SH, COOH—NH2, NH2-COOH, OH—BrCN, disulfide bond, Hydrazide-ligand with oxidized carbohydrate, protein A-antibody such as IgG, anti-mouse IgG-mouse IgG, or cleavable conjugating molecule. A capture probe may be a polynucleotide having a nucleotide sequence complementary with at least a portion of the nucleotide sequence of the polynucleotide probe, and capable of forming a hybrid with the polynucleotide probe on the surface of the magnetic particle. The portion of the polynucleotide probe that is not hybridized to the capture probe may hybridize with the target polynucleotide. In one embodiment, the probe may be biotinylated, and the magnetic particle may be a streptavidin-coated superparamagnetic bead (e.g., MyOne beads of Life Technologies, or ProMag beads from Bangs Lab).

The biomarker may be exposed to the probe shortly before or simultaneously with the application of the magnetic field. For example, the exposure may last no more than about 30, 20, 10, 5, 3, 1, 0.5 or 0.1 seconds, preferably no more than about 5 seconds, more preferably no more than about 1 second, before applying the magnetic field. A solution comprising the magnetically labeled probe may be added to the solid surface to which the biomarker is immobilized. The solution is preferably formulated suitable for hybridization of a target polynucleotide with a polynucleotide probe or specific binding of a target polypeptide with a polypeptide probe (e.g., an antibody).

A magnetic field is applied to the solution to accelerate the formation of a complex of the biomarker and the probe. The magnetic field may be of any type and may be created through electromagnetic mechanism, using a magnet or other conventional techniques known in the art. The magnetic field may be applied to the solid surface, either in a sweeping mechanism across the surface horizontally or vertically, or in a uniform fashion over the entire surface. Preferably, the magnetic field may be applied horizontally.

The application of a magnetic field may cause the probe to move towards and/or move cross over the solid surface to encounter the biomarker immobilized to the solid surface. The magnetic field may be applied for a period of time sufficient for the biomarker and the probe to form a complex, for example, no more than about 5 minutes, 1 minute, or 30, 10, 5, 1, 0.5 or 0.1 seconds, preferably no more than about 1 second.

After the magnetic field is withdrawn or inactivated, probes that have not formed complex with the biomarkers remain in the solution, which is subsequently removed. In one embodiment, magnetically labeled oligonucleotide probes in a hybridization solution may be brought in contact with target oligonucleotides immobilized to an EZTag for hybridization. A neodymium magnet may be moved horizontally underneath the EZTag to facilitate hybridization of the target oligonucleotides and the oligonucleotide probes in the EZTag, and then moved away from the EZTag after hybridization. The hybridization solution comprising magnetically labeled oligonucleotide probes not hybridized with the target oligonucleotides (i.e., unbound magnetically labeled oligonucleotide probes) is then removed from the EZTag (FIG. 2).

Figure 3:
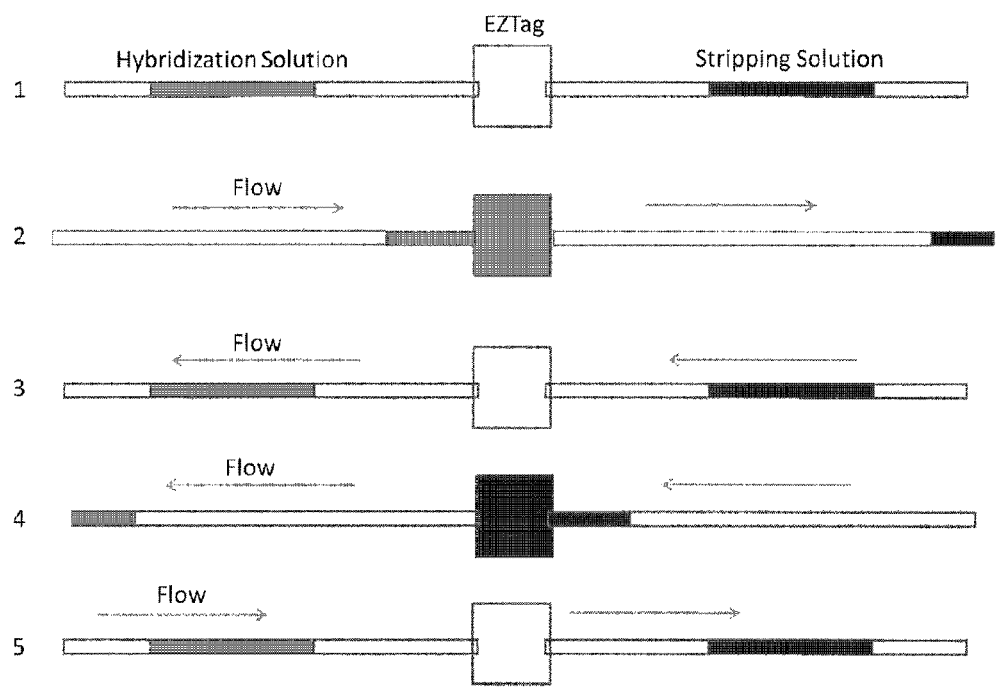
FIG. 3 is a schematic diagram illustrating fluid movement of a hybridization solution and a stripping solution in response to a magnetic field created by a magnet in a microfluidic device during a 5-step cycle. The microfluidic device comprises two channels lining up horizontally and connected with a chamber comprising an EZTag having an array of spots each containing a target oligonucleotide, one channel on the left and the other channel on the right of the chamber. Step 1: The magnet is placed away from the chamber and channels. The hybridization solution is sitting in the left channel and the stripping solution is sitting in the right channel, both away from the chamber; Step 2: The magnet is moved towards and finally beneath the chamber. The hybridization solution flows towards the EZTag and fills the chamber while the stripping solution flows away from the EZTag; Step 3: The magnet is moved away from the chamber. The hybridization solution flows away from the chamber, leaving only magnetic probes bound to the target oligonucleotides on the EZTag in the chamber. The stripping solution flows closer to the chamber; Step 4: The magnet is moved further away from the chamber. The stripping solution flows and fills the chamber. The hybridization solution flows further away from the chamber; Step 5: The magnet is moved towards the chamber to where it is in step 1. The stripping solution flows back to where it is in step 1. The hybridization solution flows back to where it is in step 1.

In another embodiment, detection of target oligonucleotides may be carried out in a microfluidic device (FIG. 3). The microfluidic device may comprise a chamber and two channels. The device may further comprise a motor controller, a micro motor, an LED light, a syringe pump, a magnet and associated gears, two small reservoirs for solutions, four pieces of tubing, and a plastic housing to host the parts. The fluid movement in the device may be controlled by the syringe pump, which may in turn be controlled by the movement of the magnet. Movement of the magnet towards the EZTag in the chamber may put the magnetically labeled oligonucleotide probes in a hybridization solution in contact with the target oligonucleotides immobilized to an EZTag, move the stripping solution further away from the chamber, and facilitate hybridization of the target oligonucleotides with the polynucleotide probes in the EZTag. Then, reverse movement of the magnet away from the EZTag may move unbound magnetically labeled oligonucleotide probes in the hybridization solution from the chamber and deliver the stripping solution into the chamber of the EZTag. Lastly, withdrawing the magnetic field by removing the magnet may move the stripping solution away from the chamber.

The signal of the complexes of the biomarkers and the probes may be then detected using various means. Many signal detection technologies routinely used in biomedical research and development, such as fluorescent labeling, colorimetric labeling, and magnetic labeling, may be implemented in signal detection. Preferably, the complex is detected visually. A signal detection module may be used to detect colorimetric labeling. Upon hybridization of a target polynucleotide with a polynucleotide probe, areas having hybridization become darker than areas without hybridization. The signal detection module may use a camera such as the one on a cell phone to capture the image of hybridization on the solid surface, process the image using an imaging processing software, and translate the hybridization signal into data in digital format. The data may then be sent to a data processing unit, which may be either as a part of a reader or at a remote location through wired or wireless connection. The data may then be verified or authenticated, and signal of true or false may be sent back to the data processing unit, which may in turn display such information to the user.

Figure 4:
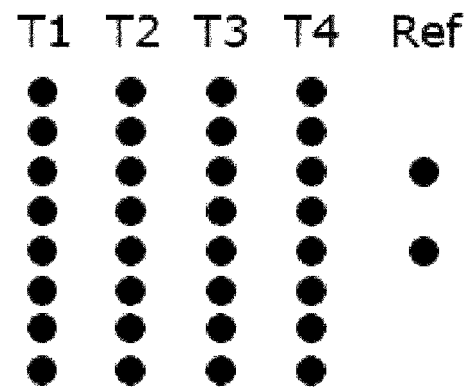
FIG. 4 shows an array of 34 giant magnetoresister (GMR) sensors in a magnetic signal detection module, including a 4×8 GMR sensor array that matches the array of target oligonucleotide spots on an EZTag in FIG. 1, and two reference sensors.

In some embodiments, a magnetic signal detection module may comprise an array of giant magnetoresister (GMR) sensors that matches the array of spots on the EZTag (FIG. 4). Two GMR sensors (labeled as "Ref" in FIG. 4) at the side of the array may serve as the reference sensors. The presence of a labeled probe in a magnetic field may induce a GMR effect, which is captured by an integrated circuit board, compared with the reference sensors, and interpreted by software loaded on a handheld device as binary code "1". The absence of a labeled probe may be interpreted as binary code "0". Together with the locations of the labeled probes in the array, these binary codes may be further interpreted by software loaded on a handheld device to produce digital readout for the EZTag.

According to the detection method of the present invention, a biomarker is detected instantaneously. The term "detecting instantaneously" as used herein refers to detecting the presence of the biomarker based on the presence of the complex of the biomarker and the probe within a very short period of time, for example, no more than about 5 minutes, 1 minute, or 30, 10, 5, 1, 0.5 or 0.1 seconds, preferably no more than about 5 seconds, more preferably no more than 1 second, after exposing the biomarker to the probe.

The instantaneous detection method of the present invention may be used for various purposes. For example, the present instantaneous detection method may be used to authenticate a product, including a pharmaceutical drug. It may also be used in a diagnostic test to detect the presence of pathogens, biological weapons, tumor antigens, or biomarkers; improve the performance of DNA-based computing platforms; and accelerate a PCR reaction, microarray-based gene expression profiling, or hybridization-based DNA/RNA sequencing. It may further be used to develop novel encryption/decryption devices using DNAs. For example, a DNA tag may serve as a security token.

For each detection method of the present invention, a kit is provided for carry out the method. The kit may comprise the probe having a magnetic label and the solution.

For each detection method of the present invention, a device is provided for carry out the method. The device may comprise a binding module, a magnetic module, and a detection module. The biomarker and the probe may form the complex in the binding module. The magnetic module may be used to apply or activate and withdraw or inactivate the magnetic field. The detection module may be used to detect the complex of the biomarker and the probe on the solid surface.

The term "about" as used herein, when referring to a measurable value such as an amount, a percentage, and the like, is meant to encompass variations of ±20%, ±10%, more preferably ±5%, even more preferably ±1%, and still more preferably ±0.1% from the specified value, as such variations are appropriate.

EXAMPLE 1

Instantaneous Detection

Instantaneous detection of target oligonucleotides T1-T4 by hybridization with oligonucleotide probes P1-P4 will be illustrated in the construction of an EZTag and subsequent hybridization on EZTag. To construct an EZTag, a 4×8 array of spots will be set up on a solid surface, containing T1, T2, T3 or T4 (represented by filled circles), or not containing T1, T2, T3, or T4 (represented by unfilled circles) in one of the four columns as indicated on top of columns (FIG. 1, left panel). A binary code will indicate the presence or absence of T1, T2, T3, or T4 in the four spots in each row (FIG. 1, right panel). The sequences of T1-T4 and P1-P4 are set forth in Table 1. 20 µM amino modified oligonucleotides (MWG/Operon, AL), dissolved in 150 mM $Na_2HPO_4$, pH8.5, will be spotted according to the filled circles in the left panel of FIG. 1 on an epoxy-coated glass slide (Corning, N.Y.) using a manual microarrayer (VP scientific, Calif.) or by hand. 50 ml of 5× SSC having 0.1% SDS and 0.1 mg/ml BSA will be used to remove unbound oligonucleotide probes and to block nonspecific binding sites on the slide, which will be covered and sealed.

TABLE 1

Oligonucleotide Sequences for Targets and Probes

| Target/Probe | Sequence | Sequence ID No. |
|---|---|---|
| T1 | ATCTCGGTACAGTGCGATAGACGC | 1 |
| T2 | TATCGCTGCAGTACGAGATAGGCC | 2 |
| T3 | CTGTGTCGAGACCATTAGACGGAC | 3 |
| T4 | TCTGTAACGACGGTAGTACGCAGC | 4 |
| P1 | GCGTCTATCGCACTGTACCGAGAT | 5 |
| P2 | GGCCTATCTCGTACTGCAGCGATA | 6 |
| P3 | GTCCGTCTAATGGTCTCGACATAG | 7 |
| P4 | GCTGCGTACTACCTGCGTTACAGA | 8 |

500 pmol of each of probes P1-P4 will be coupled to 100 µl 10 mg/ml commercially available streptavidin-coated superparamagnetic beads (e.g., MyOne beads of Life Technologies) through a biotin-streptavidin moiety, following the protocol provided by the manufacturer (e.g., Life Technologies). The probe-bound beads will be suspended in a hybridization solution having 10% formamide, 5× SSC, 0.1% SDS, 0.1 mg/ml Calf Thymus DNA at room temperature. The hybridization solution containing the probe-bound beads will be applied to the array using a pipette or a syringe pump. A magnetic field will be created by using a neodymium magnet and applied to the hybridization solution.

The application of the hybridization solution to the EZTag and the application of the magnetic field to the hybridization solution will take place at the same time or with a small time interval such as half a second, with the magnetic field applied following the application of hybridization solution. The magnetic field will be applied across the solid surface horizontally for half a second to a second before withdrawing. The hybridization solution will be removed at the same time when or after the magnetic field is withdrawn. After that, the hybridization signal, represented by darkened areas on the EZTag where the surface-attached T1, T2, T3, or T4 will be bound to the streptavidin-coated superparamagnetic beads through P1, P2, P3, or P4, respectively, and will be detectable visually by naked eyes. A digital camera, or smart cell phone equipped with a digital camera, may be used to record the image of the hybridization signal. The hybridization signal will correlate with the filled circles in the left panel of FIG. 1. The binary codes as shown in the right panel of FIG. 1 will be generated within 5 seconds after the application of the hybridization solution to the EZTag.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for detecting a biomarker immobilized to a solid surface, comprising
   (a) exposing the biomarker to a probe having a magnetic label in a solution;
   (b) moving the probe towards and horizontally across the solid surface by applying a magnetic field to the solution, whereby a complex is formed on the solid surface by the biomarker and the probe;
   (c) withdrawing the magnetic field;
   (d) removing the solution from the solid surface; and
   (e) detecting the complex, wherein the presence of the complex on the solid surface indicates the presence of the biomarker.

2. The method of claim 1, wherein the biomarker comprises a target polynucleotide having a first nucleotide sequence, wherein the probe is a polynucleotide probe comprising a second nucleotide sequence complementary with the first nucleotide sequence, and wherein the complex comprises a hybrid of the target polynucleotide and the polynucleotide probe.

3. The method of claim 1, wherein the target polynucleotide comprises 8-50 nucleotides.

4. The method of claim 1, wherein the biomarker comprises a target polypeptide, and wherein the probe is a polypeptide probe that binds specifically to the target polypeptide.

5. The method of claim 4, wherein the polypeptide probe is an antibody that binds specifically to the target polypeptide.

6. The method of claim 1, wherein the probe is attached to a particle comprising a magnetic material, and wherein the particle has a diameter ranging from 1 nm to 100 µm.

7. The method of claim 1, wherein the probe is attached to a particle comprising a magnetic material, and wherein the probe is attached to the particle via a linker.

8. The method of claim 1, wherein the probe is attached to a particle comprising a magnetic material, and wherein the probe is biotinylated, and wherein the particle is a streptavidin-coated superparamagnetic bead.

9. The method of claim 1, wherein the magnetic field is applied horizontally or vertically across the solid surface, or in a uniform fashion over the solid surface.

10. The method of claim 1, wherein the magnetic field is applied horizontally across the solid surface.

11. The method of claim 1, wherein the magnetic field is applied for no more than 5 seconds.

12. The method of claim 1, wherein the complex is detected visually.

13. The method of claim 1, wherein the biomarker is detected no more than 5 seconds after the exposure.

14. The method of claim 1, wherein the biomarker is obtained from a biological sample.

15. The method of claim 1, wherein the biomarker is on a product.

16. The method of claim 15, wherein the product is a pharmaceutical product.

17. The method of claim 16, wherein the pharmaceutical product is a drug.

18. The method of claim 15, further comprising authenticating the product, wherein the presence of the biomarker on the product indicates that the product is authentic.

19. The method of claim 1, wherein the biomarker is detected no more than 5 minutes after exposing the biomarker to the probe.

20. The method of claim 1, further comprising striping the probe from the solid surface.

* * * * *

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
atctcggtac agtgcgatag acgc                                      24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
tatcgctgca gtacgagata ggcc                                      24

<210> SEQ ID NO 3
<211> LENGTH: 24
<212> TYPE: DNA
<213> ORGANISM: Artificial Sequence -continued

```
<220> FEATURE:
<223> OTHER INFORMATION: Synthetic

<400> SEQUENCE: 3
ctgtgtcgag accattagac ggac                                      24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tctgtaacga cggtagtacg cagc                                      24

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
gcgtctatcg cactgtaccg agat                                      24

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
ggcctatctc gtactgcagc gata                                      24

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
gtccgtctaa tggtctcgac atag                                      24

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
gctgcgtact acctgcgtta caga                                      24
```